United States Patent
Snyder

(10) Patent No.: US 6,664,237 B1
(45) Date of Patent: Dec. 16, 2003

(54) ORAL TREATMENT OF COMPANION ANIMALS WITH ECTOPARASITICIDAL SPINOSYNS

(75) Inventor: Daniel Earl Snyder, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 8 days.

(21) Appl. No.: 10/049,345

(22) PCT Filed: Aug. 2, 2000

(86) PCT No.: PCT/US00/19557

§ 371 (c)(1),
(2), (4) Date: Jan. 24, 2002

(87) PCT Pub. No.: WO01/11963

PCT Pub. Date: Feb. 22, 2001

Related U.S. Application Data

(60) Provisional application No. 60/148,618, filed on Aug. 12, 1999.

(51) Int. Cl.$^7$ .......................... A01N 43/04; C07H 17/08
(52) U.S. Cl. ........................ 514/28; 514/329; 514/355; 536/7.1; 536/17.2
(58) Field of Search .............................. 514/329, 355, 514/548; 536/7.1, 17.2

(56) References Cited

U.S. PATENT DOCUMENTS

| | | |
|---|---|---|
| 5,145,684 A | 9/1992 | Liversidge et al. |
| 5,202,242 A | 4/1993 | Mynderse et al. |
| 5,227,295 A | 7/1993 | Baker |
| 5,362,634 A | 11/1994 | Boeck et al. |
| 5,496,931 A | 3/1996 | Boeck et al. |
| 5,539,089 A | 7/1996 | Broughton et al. |
| 5,571,901 A | 11/1996 | Boeck et al. |
| 5,591,606 A | 1/1997 | Turner et al. |
| 5,631,155 A | 5/1997 | Turner et al. |
| 5,670,364 A | 9/1997 | Mynderse et al. |
| 5,670,486 A | 9/1997 | Mynderse et al. |
| 5,767,253 A * | 6/1998 | Turner et al. ............ 536/6.5 |
| 5,840,861 A | 11/1998 | Mynderse et al. |
| 6,001,981 A * | 12/1999 | DeAmicis et al. ........ 536/7.1 |
| 6,063,771 A | 5/2000 | Snyder |
| 6,342,482 B1 | 1/2002 | Snyder |

FOREIGN PATENT DOCUMENTS

| | | |
|---|---|---|
| EP | 0 375 316 | 6/1990 |
| WO | WO 97/00265 | 1/1997 |
| WO | WO 97/33471 | 9/1997 |
| WO | WO 00/60940 | 10/2000 |
| WO | WO 01/11961 | 2/2001 |
| WO | WO 01/12156 | 2/2001 |
| WO | WO 01/19840 | 3/2001 |
| WO | WO 01/40446 | 6/2001 |

OTHER PUBLICATIONS

Agricultural Chemical News, 195(2), "NAF–85 (spinosad): DowElanco insecticide" (1995).
Agriculture Chemical News, 186(2), "Spinosad, NAF–144; DowElanco seeks EPA approval for insecticide" (1995).
Spencer, et al., "Spinosad insect control agent; lack of effects in a one year neurotoxicity screening study in rats," Fundam. Appl. Tocicol.; Pt. 2, 211, 30(1) (1996).
Kirst, et al., "Chemistry of Biology of the spinosyns a new class of naturally derived insect control agents," Abstracts of Papers Americal Chemical Society; 210$^{th}$ American Chemical Society, 210, Part 1, Abstract No. AGR0061.
Adan, et al., "Laboratory evaluation of the novel naturally derived compound spinosad against ceratitis capitata," Pesticide Science, 48(3), pp. 261–268 (1996).
Boyd, Impact of insecticides on predators of the soybean looper, pseudoplusia inc, PhD Dissertation, The Louisiana State University and Agricultural and Mechanical Col., UMI(9637762).
King, et al., Spinosad bait for the Caribbean fruit fly (Kiptera: Tephritidea), Florida Entomologist, 79(4) ppg. 526–531 (1996); ISSN: 0015–4040.
Magnussen, et al., "Characterization of spinosad related residues in poultry tissues and eggs following oral administration," 211$^{th}$ American Chemical Society National Meeting, New Orleans, Louisiana, USA, 211:1–2; AGRO 43; ISSN 0065–7 (1996).
Saunders, et al., "Degradation of spinosad in aqueous solution," 211$^{th}$ Americal Chemical Society National Meeting, New Orleans, Louisiana, USA, 211, Part 1, Abstract No. AGR0048.
Sparks, et al., "Chemistry and biology of the spinosyns: components of spinosad (Tracer), the first entry into DowElanco's naturalyte class of insect control products," Proc.—Beltwide Cotton Conf., 2:692–696 (1996); ISSN: 1059–2644.
Burton, et al., "Tracer naturalyte insect control physical property attributes," Proc.—Beltwide Cotton Conf., 2:696–697 (1996); ISSN: 1059–2644.
Thompson, et al., "Spinosad and the new naturalyte insect control class," Proc.—Beltwide Cotton Conf., 2:870–872 (1996); ISSN: 1059–2644.

(List continued on next page.)

Primary Examiner—James O. Wilson
Assistant Examiner—Traviss McIntosh
(74) Attorney, Agent, or Firm—John C. Demeter

(57) ABSTRACT

The invention provides single-dose oral formulations for controlling an ectoparasite infestation on a companion animal for a prolonged time, said formulations comprising a spinosyn component, or a physiologically acceptable derivative or salt thereof, and a carrier in oral dosage form. It also provides methods for controlling such infestations comprising orally administering a single dose of these formulations to the animal.

7 Claims, No Drawings

OTHER PUBLICATIONS

Murray, et al., "The effects of spinosad (Tracer) on pests and beneficials," *Australian Cottongrower*, 18:62–64 (1997).

Heller, et al., "Evaluation of experimental DowElanco NAF85 and NAF127 formulations, and Dursban Pro for management of black cutworm on creeping bentgrass, 1996," *Anthropod Management Tests*, 22:345 (1997).

Heller, et al., "Evaluation of NAF formulations, Dursban Pro, and Scimitar CS for management of black cutworm on creeping bentgrass, 1995," *Arthropod Management Tests*, 22:346 (1997).

Salgado, et al., "Studies on the mode of action of spinosad, the active ingredient in Tracer insect control," *Proc.—Beltwide Cotton Conference*, 2:1082–1084 (1997); ISSN: 1059-2644.

Murrey, et al., "The effect of spinosad (Tracer) on arthropod pest and beneficial populations in Australian cotton," *Proc.—Beltwide Cotton Conf.*, 2:1087–1091 (1997); ISSN: 1059-2644.

Sparks, et al., "Penetration and metabolism of spinosyn A in lepidopterous larvae," *Proc.—Beltwide Cotton Conference*, 2:1259–1264 (1997); ISSN: 1059-2644.

*Agricultural Chemical News*, "Success (spinosad): a new DowElanco insecticide formulation," 209: pp. 2–15 (1997).

*Agricultural Chemical News*, "Tracer (spinosad): Dow-Elanco gains insecticide registration," 211; pp. 3–15 (1997).

*Agricultural Chemical News*, "Success (spinosad): Dow-Elanco gains 24(c) insecticide label to use in California," 213; pp. 2–15 (1997).

*Agricultural Chemical News*, "Conserve SC (spinosad): DowElanco gains EPA, USA, insecticide registration," 215; pp. 1–15 (1997).

Yeh, et al., "Application of empore disc extraction for trace analysis of spinosad and metabolites in leafy vegetables, pepper, and tomatoes by high-performance liquid chromtography with ultraviolet detection," *Journal of Agricultural and Food Chemisry*, vol. 45, No. 5, pp. 1746–1751; ISSN 0021-8561.

Boyd, et al., "Residual toxicity of selected insecticides to heteropteran predaceous species (Heteroptera: Lygaeidae, Nabidae, Pentatomidae) on soybean," *Environ. Entomol.*, vol. 27, No. 1, pp. 154–160 (1998).

Kolarid, et al., "Colorado potato beetle control, 1997," *Arthropod Management Tests*, vol. 23; pp. 124–126 (1998).

Cowles, "Effect of spinosad formulations and other miticides on twospotted spider mite, 1995," *Arthopod Management Tests*, vol. 23; pp. 342–343 (1998).

Kjaer, et al., "The impact of phenology, exposure and instar susceptibility on indecticide effects on a chrysomelid beetle population," *Prestic. Sci.*, vol. 52, No. 4, pp. 361–371 (1998).

Marty, et al., "The maternal and developmental toxicity of spinosad in Sprague–dawley rats and New Zealand White rabbits," *Teratology*, vol. 57, pp. 4–5 (1998).

Salgado, et al., "Studies on the mode of action of spinosad: The internal effective concentration dependence of neural excitation," *Pesticide Biochemistry and Physiology*, vol. 60, No. 2, pp. 103–110 (1998).

Boyd, et al., "Susceptibility of predaceous hemipteran species to selected insecticides on soybean in Louisiana," *Journal of Economic Entomology*, vol. 91, No. 2, pp. 401–409 (1998).

Woodburn, et al., "Bioconcentration and metabolism of a unique insecticide (spinosyn) by the Rainbow trout," *Second World Congress of the Society of environmental toxicology and chemi*,PT127; pp. 5–9 (1995).

Stoltz, et al., "Colorado potato beetle control with foliar sprays, 1995," *Arthropod Management Tests*, vol. 21, pp. 168–169.

Sewell, et al., "Irish potato, control of Colorado potato beetle, 1995," *Arthropod Management Tests*, vol. 21, pp. 158–159.

Olson, et al., "Potato, Colorado potato beetle control with spinosad, 1995," *Arthropod Management Tests*, vol. 21; pp. 154–155.

Noetzel, et al., "Control of resistant Colorado potato beetle, Blaine, MN, 1995," *Arthropod Management Tests*, vol. 21, p. 149.

Noetzel, et al., "Colorado potato beetle control, Crookston, MN, 1995," *Arthropod Management Tests*, vol. 21, pp. 145–146.

Hedin, et al., "Physical and biological properties of the spinosyns: novel macrolide pest–control agents from fermentation," Phytochemicals for Pest Control, Chapter 11, 1995 *International Chemical Congress of Pacific Basin Societies*; ACS Symposium Series 658, pp. 144–153.

Boyd, "Impact of insecticides on predators of the soybean looper, Pseudoplusia inc," *Dissertation*; UMI (9637762) : [97pp] ; The Louisiana State University and Agriculture.

Sears, et al., "Effects of various rates and combinations of insecticides on the control of Colarado potato beetle (CPB) (1995)," *Pest Management Research Report—Insects and Diseases*, ICAR: 86100104; pp. 159–161; Report No. 061 (1995).

D.P. Rainey, et al.: "The tissue distribution and metbolism of spinosyn A and D in lactating goats"; XP002153173 (found from STN–International accession No. 1996–85398 CROPU & Abstr. Pap. Am. Chem. Soc. (211 MEET., PT. 1, AGR0045, 1996).

Boech, et al., Chemical Abstracts, 114, 9, Abstract No. 80066m (1991).

Kirst, et al., "Discovery Isolation, and Structure Elucidation of a Family of Structurally Unique, Fermentation–Derived Tetracyclic Macrolides," ACS Symposium Series, Snythesis and Chemistry of Agrochemicals III, 504, pp. 214–225 (1992).

Crouse, et al., "Naturally Derived Materials as Products and Leads for Insect Control: The Spinosyns," Rev. Toxicol, 2, pp. 133–146 (1998).

Mertz, F. P., et al., "Saccharopolyspora spinosad sp. Nov. Isolated from Soil Collected in a Sugar Mill Rum Still," Int. J. System Bacteriol, 40, pp. 34–39 (1990).

Salgado, V. L., "Studies on the Mode of Action of Spinosad: Insect Symptoms and Physiological Correlates," Pestic. Biochem. Physiol., 60, pp. 91–102 (1998).

Thompson, G. D., et al., "Spinosad A Case Study: An Example from a Natural Products Discovery Programme," Pest. Manag. Sci., 56, pp. 696–702 (2000).

Thompson, G. D., "The Discovery of Saccharopolyspora spinosad and a New Class of Insect Control Products," Down to Earth, 52, pp. 1–5 (1997).

Breuninger, J. M., "Conserved SC: A New Product for the Turfgrass and Ornamental Industry," Down to Earth, 53, pp. 1–5 (1998).

Nolting, S. P., "Insect Control in Cotton with Tracer," Down to Earth, 52, pp. 21–27 (1997).

Sparks, et al., "Biological Activity of the Spinosyns, New Fermentation Derived Insect Control Agents, on Tobaco Budworm (Lepidopters: Noctuidae) Larvae," J. Econ. Entomol., 91, pp. 1277–1283 (1996).

Kirst, et al., Tetrahydron Letters, 32(37), 4839–4842 (1991).

Snyder, et al., J. Am. Chem. Soc., 106, 787–789 (1984).

T. C. Sparks, et al., "Biological Characteristics of the Spinosyns: A New Naturally Derived Insect Control Agents," Cotton Insect Research and Control Conference, 1995 Beltwide Cotton Conferences, pp. 903–907.

G. D. Thompson, "Spinosyns: An Overview of New Natural Insect Management Systems," Cotton Insect Research and Control Conference, 1995 Beltwide Cotton Conferences, pp. 1039–1043.

* cited by examiner

US 6,664,237 B1

ORAL TREATMENT OF COMPANION ANIMALS WITH ECTOPARASITICIDAL SPINOSYNS

This application claims the benefit of provisional application No. 60/148,618 filed Aug. 12, 1999.

Companion animals, including but not limited to dogs, cats, and horses, are an increasingly important part of today's society. They provide pleasure and companionship to human friends, which leads to what has been termed the human-animal bond. Unfortunately, a number of insect pests and parasites can infest or infect these animals. Such pests include, for example, fleas, lice, mosquitoes, mites, ticks and certain fly species. Safe, effective ways to eliminate these pests are desired, both for the animal's well-being and for the comfort of its human associate.

The most common ectoparasites of cats and dogs worldwide are the cat and dog fleas, *Ctenocephalides felis felis* and *Ctenocephalides canis*, respectively. Interestingly, the cat flea very commonly infests dogs. Fleas annoy the animal it infests and the pet's owner. Frequently, fleas cause more serious problems by inducing flea-allergy dermatitis. It has been estimated that flea-related diseases account for over 50% of the dermatological cases reported to veterinarians [D. E. Bevier-Tournay, "Flea and Flea Control" *Curr. Vet. Therapy* 10: 586–592 (1989)]. In addition, the cat flea is known to transmit tapeworms in dogs and has been implicated in the transmission of cat scratch disease and murine typhus. Other pests of companion animals, such as ticks and mosquitoes, are also known to transmit disease. For example, ticks are known to transmit bacterial and viral diseases; and mosquitoes can infect dogs and cats with the filarial nematode that causes heartworm disease.

Furthermore, economic expenses involved in flea control are high. In the United States, for example, pet owners spend over $1 billion dollars for flea control products annually [R. Conniff, "When It Comes to Pesky Flea, Ignorance is Bliss," *Smithsonian*: 26: 76–85 (1995)].

Treatments currently available achieve varying degrees of success. Most treatments involve chemicals applied to indoor and outdoor surfaces, as well as to the pet. The chemicals used include a variety of carbamates, organophosphates, pyrethrins and pyrethroids. These compounds often have toxic side effects that are a problem for both the pet and its owner. For example, concentrated forms of pyrethroids available for use on dogs are extremely toxic and lethal to cats and thus cannot and should not be used on cats. In addition, there is evidence that the use of these chemicals has led to multiple category insecticide resistance [N. K. Rust and M. W. Dryden, *Ann. Rev. Entomol.* 42: 451–473 (1997)]. Thus, there continues to be a need for relatively safe, effective agents for controlling ectoparasites on companion animals, such as cat and dog fleas.

The spinosyns (also known as A83453 factors) are agricultural insecticides that have shown activity against southern armyworm and other insects in the order Lepidoptera, and cotton aphid and other members of the order Homoptera. (See, for example, U.S. Pat. No. 5,571,901).

The spinosyns were also known to have some ectoparasiticidal activity, i.e., they had in vitro activity against mosquito larvae, black blowfly larvae and adult stable flies, which are members of the insect order Diptera, and transient systemic activity against larval blowfly and adult stable fly in guinea pigs and sheep (see U.S. Pat. No. 5,571,901, col 26–32). Although it was suggested that the spinosyns would be active against a number of ectoparasites in a number of animals by a variety of routes, there have been no subsequently reported studies to support these suggestions.

This invention came about by the discovery that spinosyns, such as spinosyn A, can provide prolonged residual control of an ectoparasite infestation on a companion animal when a single dose of a spinosyn is administered orally to the animal. Thus, the invention provides a method for prolonged control of the ectoparasite in a safer manner than that achieved with previously known treatments.

In one aspect, this invention relates to a long-acting, single-dose oral formulation for controlling an ectoparasite infestation on a companion animal, said formulation comprising an ectoparasiticidal amount of a spinosyn, or a physiologically acceptable derivative or salt thereof, and a physiologically acceptable carrier, in an oral dosage form.

In another aspect the invention relates to the use of a single, long-acting oral formulation of a spinosyn, or a physiologically acceptable derivative or salt thereof, for controlling an ectoparasite infestation on a companion animal.

It also relates to the use of a spinosyn, or a physiologically acceptable derivative or salt thereof, for the manufacture of a long-acting single-dose oral medicament for controlling an ectoparasite infestation on a companion animal.

This invention also relates to a method of controlling an ectoparasite infestation on a companion animal for a prolonged time, comprising orally administering a single dose of an effective amount of a spinosyn, or a physiologically acceptable derivative or salt thereof, to the animal. An especially useful method of this invention is a method for controlling cat or dog fleas on a companion animal for a prolonged time comprising orally administering a single dose of an effective amount of a spinosyn, or a physiologically acceptable derivative or salt thereof, to the animal.

The invention further relates to an article of manufacture, comprising packaging material and a formulation for controlling an ectoparasite infestation on a companion animal contained within said packaging material, wherein said formulation comprises an oral long-acting unit dose of an ectoparasiticidal amount of a spinosyn, or a physiologically acceptable derivative or salt thereof, and a physiologically acceptable carrier; and wherein said packaging material comprises a label or package insert with instructions for orally administering the dose to the animal.

This article of manufacture or kit is particularly appropriate when the companion animal is a dog or a cat. When the animal is a dog, the formulation contained in the packaging material will generally be in tablet form, and the label or package insert will indicate the number of tablets to be given by mouth to the dog and the timing of such administration. The timing of doses will generally be every 30 days. When the animal is a cat, the formulation contained in the packaging material will generally be a liquid formulation and the label or package insert will indicate the unit dose to be given by mouth to the cat. The timing of doses will generally be every 30 days. The contents of each kit would typically be sufficient to control the ectoparasite infestation for a period of several months.

Spinosyns are naturally derived fermentation products. They are macrolides produced by cultivation of *Saccharopolyspora spinosa*. The fermentation produces many factors, including spinosyn A and spinosyn D (also called A83543A and A8354D). Spinosyn A and spinosyn D are the two spinosyns that are most active as insecticides. A product comprised mainly of these two spinosyns is available commercially under the trade name "spinosad". The major spinosyn factor, spinosyn A, is known to have an excellent human and animal safety and toxicological profile.

Each spinosyn has a 12-membered macrocyclic ring that is part of an unusual tetracyclic ring system to which two different sugars are attached, the amino-sugar forosamine and the neutral sugar 2N,3N,4N-(tri-O-methyl)rhamnose. This unique structure sets the spinosyns apart from other macrocyclic compounds.

Spinosyn A was the first spinosyn isolated and identified from the fermentation broth of *Saccharopolyspora spinosa*. Subsequent examination of the fermentation broth revealed that *S. spinosa* produced a number of spinosyns that have been called spinosyns A to J (A83543A to J). The primary components are spinosyns A and D. Additional spinosyns, lettered from K to W, have been identified from mutant strains of *S. spinosa*. The various spinosyns are characterized by differences in the substitution patterns on the amino group of the forosamine, at selected sites on the tetracyclic ring system and on the 2N,3N,4N-(tri-O-methyl)rhamnose group.

The term "spinosyn or a derivative thereof" as used herein refers to an individual spinosyn factor (spinosyn A, B, C, D, E, F, G, H, J, K, L, M, N, O, P, Q, R, S, T, U, V, W or Y), an N-demethyl derivative of an individual spinosyn factor, or a combination thereof. For convenience, the term "spinosyn component" will also be used herein to mean an individual spinosyn, or a physiologically acceptable derivative or salt thereof, or a combination thereof.

Boeck et al. described spinosyns A–H and J (which they called A83543 factors A, B, C, D, E, F, G, H and J), and salts thereof, in U.S. Pat. Nos. 5,362,634 (issued Nov. 8, 1994); 5,496,932 (issued March 5, 1996); and 5,571,901 (issued Nov. 5, 1996). Mynderse et al. described spinosyns L–N (which they called A83543 factors L, M and N), their N-demethyl derivatives, and salts thereof, in U.S. Pat. No. 5,202,242 (issued Apr. 13, 1993); and Turner et al. described spinosyns Q–T (which they called A83543 factors Q, R, S and T), their N-demethyl derivatives, and salts thereof, in U.S. Pat. Nos. 5,591,606 (issued Jan. 7, 1997) and 5,631,155 (issued May 29, 1997). Spinosyns K, O, P, U, V, W and Y are described, for example, by Carl V. DeAmicis, James E. Dripps, Chris J. Hatton and Laura I. Karr in American Chemical Society's Symposium Series: Phytochemicals for Pest Control, Chapter 11, "Physical and Biological Properties of Spinosyns: Novel Macrolide Pest-Control Agents from Fermentation", pages 146–154 (1997).

The spinosyns can react to form salts that are also useful in the methods and formulations of this invention. The salts are prepared using standard procedures for salt preparation. For example, spinosyn A can be neutralized with an appropriate acid to form an acid addition salt. The acid addition salts of spinosyns are particularly useful. Representative suitable acid addition salts include salts formed by reaction with either an organic or inorganic acid such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

Using oral formulations of spinosyns to systemically control ectoparasites of companion animals, as a single treatment modality or in combination with other commonly used ectoparasiticidal compounds, has several advantages. Spinosad is a naturally derived fermentation product with an excellent human and animal safety profile, which is in contrast to currently used synthetic organically derived compounds such as synthetic organophosphates, pyrethroids and pyrethrins, organochlorines, and carbamates. For example, some of the currently used products such as organophosphates and synthetic pyrethroids are very toxic to cats and can be lethal.

Spinosyns also provide advantages because they are very effective against fleas, mites, ticks, lice and flies with post-treatment residual protection, depending on the dosages used. Furthermore, spinosyns have no cross-resistance to existing compounds. Thus, they are especially useful against parasite populations on companion animals that have existing levels of resistance to currently used products. Spinosyns, therefore, can be used in integrated pest management (IPM) programs to extend the life line of commonly used products where resistance is not well developed or has not yet developed.

Systemic efficacy (ingestion of blood containing spinosad by the blood feeding parasites, such as fleas) provides different mode of exposure compared to topically applied ectoparasiticides where contact with the parasite at the skin surface is the mode of exposure. The advantages of oral systemic treatments and killing of parasites from ingestion of blood, compared to topical applications and contact killing, include:

a) reduced exposure to the human applicator and children and objects in the animal's environment (e.g., flooring, carpets, furniture);

b) no worry about loss from exposure of the animal to water (lakes, streams, bathing, etc.) or from loss due to rubbing;

c) no concern about UV exposure and degradation;

d) no problems with oxidation from oils on skin, etc.; and e) assurance that the entire dose is administered (compared to a topical application where some of the dose may drip off, rub off and/or remain in the dispensing tube immediately after treatment).

The formulations of this invention may further include, in combination with the spinosyn component, one or more other compounds that have activity against the specific ectoparasite or endoparasite to be controlled, such as, for example, synthetic pyrethroids, natural pyrethins, organophosphates, organochlorines, carbamates, foramidines, avermectins, milbemycins, insect growth regulators (including chitin synthesis inhibitors, juvenile hormone analogs, and juvenile hormones), nitromethylenes, pyridines and pyrazoles.

All ratios, percentages, and parts discussed herein are "by weight" unless otherwise specified.

The term "oral formulation" means that the spinosyn component or components, either alone or in combination with one or more of the other types of compounds listed supra, is formulated into a product or formulation suitable for administering to the animal by mouth. These products or formulations include, but are not limited to, tablets, capsules, liquids, gels, pastes, oral sprays, buccal formulations, powders and chewable treats or animal feeds containing the active component or components. Generally, such formulations include a physiologically acceptable carrier. Such carriers are well known in the veterinary arts. Animal feeds are particularly useful carriers.

The term "controlling an ectoparasite infestation" refers to preventing, minimizing or eliminating an infestation by an ectoparasite. The term "ectoparasite" refers to insect and acarine pests that commonly infest or infect companion animals. Examples of such ectoparasites include the egg, larval, pupal, nymphal and adult stages of fleas, lice, mosquitoes, mites, ticks and blood-sucking, biting or nuisance fly species.

The term "companion animals" includes dogs, cats, horses, rabbits and other pets owned and maintained in close association with humans as part of the human-animal bond.

The term "single-dose formulation" means that one dose of the formulation effectively controls the ectoparasite infestation for a prolonged time. The term "prolonged time" comprises a period of at least 7 days, preferably a period of at least two weeks. The term "long-acting" means that the activity lasts for a prolonged time.

The methods of this invention are carried out by orally administering the spinosyn component to the companion animal. Oral administration may be carried out using tablets and animal feeds. For some animals, such as certain cats, administration is best accomplished by using an acceptable liquid formulation that is administered directly or added to their food ration. Especially useful methods of orally administering the spinosyn component are by administering it in chewable tablets or treats and animal feeds.

Conventional oral tablets generally consist of the spinosyn component, a diluent to assist in increasing the powder mass to a convenient size and improve compressibility, a binder to hold the compressed powder together and a lubricant to assist in densification and ejection from the tablet die. They may also contain a disintegrate to improve disintegration and dissolution as well as stabilizers, colors and flavors. Tablets are often coated to improve appearance or taste or to alter the dissolution properties. Tablets can be designed to dissolve fast or slow, and depending on the actual volume and compressibility of the drug, large or small. They can be made chewable or to dissolve under the tongue or in the pouch of the cheek.

Conventional liquid formulations for oral administration are usually solutions, suspension or emulsions of the spinosyn component together with suitable diluents, solvents, flavors and colors to make a palatable dosage form. Other materials to complex, adjust pH, and improve mouth feel are also often used.

In carrying out the methods of this invention, an effective amount of a spinosyn, or a physiologically acceptable derivative or salt thereof, is administered orally to the companion animal. The terms "effective amount" and "ectoparasiticidal amount" refer to the amount needed to control the particular ectoparasite infestation. As those in the art will understand, this amount will vary depending upon a number of factors. These factors include, for example, the type of companion animal being treated, its weight and general physical condition and the type of ectoparasite to be controlled.

In general, an effective amount refers to a dose of from about 1 to about 100 mg of the spinosyn/kg of body weight of the companion animal. More commonly, the effective amount is from about 10 to about 50 mg/kg of body weight of the animal.

Tablet formulations will typically contain from about 1 to about 75 percent of spinosyn component or components (by weight) in the tablet. Animal feeds will typically contain from about 0.1 to about 10 percent of spinosyn component or components (by weight) in the feed.

The following examples illustrate the methods of this invention:

EXAMPLE 1

Efficacy of Spinosad Administered per os to Dogs for the Treatment and Control of *Ctenocephalides felis*

Methods: Nine random-source dogs of both sexes and various ages were used in this study. The dogs were housed individually in concrete-floored chain-link runs during the study period and were fed a commerical dry dog food ration with ad libitum access to water. The dogs were allocated to each of the 3 treatment groups (3 dogs per group) based on their pre-treatment flea counts from experimental infestations.

Each dog received one or more gelatin capsules containing technical active spinosad powder by mouth. They were dosed at either 50 or 100 mg/kg body weight on day 0. Each dog was fed approximately one-half can of moist dog food just prior to and just after receiving their individual doses. Each dog was experimentally infested with ~100 unfed adult fleas on test days −1, 0, 6, 13, 20, 27, 34, 41, and 48. Comb counts for live adult fleas were conducted ~24 hours following each of the subsequent experimental infestations, i.e., on test days 0 (8 hours post-treatment), 1, 7, 14, 21, 28, 35,42 and 49.

Results: Geometric Mean Percent reduction in live adult flea counts compared to untreated control group in dogs treated orally with spinosad are listed below in Table 1.

TABLE 1

Geometric Mean Percent Reduction in Live Adult Flea Counts in Dogs Treated With Spinosad Compared to Untreated Control Group

| Dose of Spino- | Days Post-treatment | | | | | | | | |
|---|---|---|---|---|---|---|---|---|---|
| sad | 8 hrs | D1 | D7 | D14 | D21 | D28 | D35 | D42 | D49 |
| 50 mg/kg | 97.4 | 100 | 99.3 | 99.7 | 99.5 | 95.0 | 78.1 | 69.9 | ND[a] |
| 100 mg/kg | 98.9 | 100 | 100 | 100 | 99.5 | 99.7 | 99.4 | 97.5 | 94. |

[a]ND: not determined

No adverse reactions were seen.

EXAMPLE 2

Efficacy of Spinosad Administered per os to Dogs for the Treatment and Control of Brown Dog Ticks (*Rhipicephalus sanguineus*) and Cat Fleas (*Ctenocephalides felis*)

Methods: Twelve random-source dogs of both sexes and various ages were used in the study. The dogs were housed, fed, and watered as in Example 1. The dogs were allocated to each of the 3 treatment groups (4 dogs per group) based on their pre-treatment tick counts from experimental infestations. Each dog received by mouth one or more gelatin capsules containing either nothing (control) or technical active spinosad powder. The spinosad-treated groups were dosed at either 50 or 100 mg/kg body weight on day 0. Each dog was fed approximately one-half can of moist dog food just prior to and just after receiving their individual capsules. Each dog was infested with ~50 unfed adult ticks on test days —1, 7, 14, 21 and 28. Each dog was also concurrently infested with ~100 unfed adult fleas on test days −1, 7, 14, 21, 28, 35 and 42. Comb counts for live adult fleas and ticks were conducted ~48 hours following each of the experimental infestations (i.e., on test day 1) and on post-treatment days 9, 16, 23 and 30 for both ticks and fleas and additionally on days 37 and 44 (for fleas only).

Results: Geometric Mean Percent reduction in live adult flea counts compared to untreated control group in dogs treated orally with spinosad are listed below in Table 2.

TABLE 2

Geometric Mean Percent Reduction in Live
Adult Flea Counts in Dogs Treated with
Spinosad Compared to Untreated Control Group

| Dose of Spinosad | Days Post-treatment | | | | | | |
|---|---|---|---|---|---|---|---|
| | 1 | 9 | 16 | 23 | 30 | 37 | 44 |
| 50 mg/kg | 100 | 100 | 99.75 | 98.3 | 92.5 | 93.6 | 63.1 |
| 100 mg/kg | 100 | 100 | 100 | 100 | 100 | 98.9 | 97.3 |

Geometric Mean Percent reductions in live adult tick counts compared to untreated control group in dogs treated orally with spinosad are listed in Table 3.

TABLE 3

Geometric Mean Percent Reduction in Live
Adult Tick Counts in Dogs Treated with
Spinosad Compared to Uutreated Control Group

| Dose of Spinosad | Days Post-treatment | | | | |
|---|---|---|---|---|---|
| | 1 | 9 | 16 | 23 | 30 |
| 50 mg/kg | 94.8 | 67.8 | 49.1 | 52.1 | 5.0 |
| 100 mg/kg | 97.2 | 91.5 | 70.6 | 79.7 | 71.3 |

Summary of Results (both examples): Orally administered spinosad was able to provide excellent immediate knockdown and long term post-treatment residual control of fleas on dogs. The 50 mg/kg dose provided greater than 90% flea efficacy through day 37 of the study. The 100 mg/kg dose provided greater than 90% flea efficacy through day 49 of the study (when the study was terminated).

Orally administered spinosad also was able to provide excellent immediate knockdown and a moderate length of post-treatment residual control of ticks on dogs. The 50 mg/kg dose provided greater than 90% tick efficacy through day 1 of the study. The 100 mg/kg dose provided greater than 90% tick efficacy through day 9 of the study.

EXAMPLE 3

Efficacy of Spinosad Administered per os to Dogs
for the Treatment and Control of Fleas
(*Ctenocephalides felis*)

Methods: Thirty-two (32) random source dogs of both sexes and various ages were used in the study to evaluate different dosages and physical forms of spinosad and their impact on oral efficacy against fleas. The dogs were housed individually in concrete-floored chain-link runs during the study period and were fed a commercial dry dog food ration with ad libitum access to water. The dogs were allocated to each of the 8 treatment groups (4 dogs per group) based on their pre-treatment flea counts from experimental infestations. Each dog received by mouth one or more gelatin capsules containing technical spinosad in the different physical forms and dosages listed infra. They were dosed based on body weight on day 0. Each dog was fed approximately one-half can of moist dog food just prior to, and just after, receiving their individual gelatin capsules containing the specific spinosad formulation and dosage. Each dog was experimentally infested with ~100 unfed adult fleas on test days −1, 2, 6, 9, 13, 20, 27 and 34. Comb counts for live adult fleas were conducted ~24 hours following dosing or each of the subsequent experimental infestations (i.e.—test days 1, 3, 7, 10, 14, 21, 28 and 35).

Treatments:

| Treatment No. | Oral Dose (mg/kg) | Formulation Type & Concentration |
|---|---|---|
| 1 | 11.25 | Milled spinosad, tecnnical, in gelatin capsules |
| 2 | 22.5 | Milled spinosad, technical, in gelatin capsules |
| 3 | 45 | Milled spinosad, technical, in gelatin capsules |
| 4 | 22.5 | Amorphous spinosad, technical, in gelatin capsules |
| 5 | 22.5 | Unmilled spinosad, technical, in gelatin capsules |
| 6 | Untreated control | None |

TABLE 4

Geometric Mean Percent Reduction in Live
Adult Flea Counts Compared to Untreated Control
Group in Dogs Treated Orally with Spinosad

| Treatment No. | Days Post-Treatment | | | | | | | |
|---|---|---|---|---|---|---|---|---|
| | 1 | 3 | 7 | 10 | 14 | 21 | 28 | 35 |
| 1 | 100.0 | 99.6 | 94.4 | 96.0 | 87.0 | 74.7 | 71.4 | 31.8 |
| 2 | 100.0 | 100.0 | 100.0 | 99.6 | 99.0 | 91.9 | 78.5 | 50.95 |
| 3 | 100.0 | 100.0 | 100.0 | 100.0 | 99.8 | 99.5 | 98.9 | 94.2 |
| 4 | 100.0 | 100.0 | 100.0 | 100.0 | 100.0 | 97.8 | 91.4 | 56.1 |
| 5 | 100.0 | 100.0 | 100.0 | 100.0 | 100.0 | 99.3 | 98.9 | 60.4 |

Summary: Orally administered spinosad provided excellent immediate knockdown efficacy (99.6 to 100% on days 1 & 3 post-treatment) and also good-to-excellent long term post-treatment residual control of fleas on dogs. The 45 mg/kg milled spinosad dose provided greater than 94% flea efficacy through day 35 of the study. The lower dosages of milled spinosad provided shorter post-treatment residual control based on the dose. The adult flea efficacy of the ~22.5 mg/kg spinosad dosages of milled (mean particle size of ~5 microns), amorphous (non-crystalline), and unmilled (mixture of particles sizes greater than 5 microns with a distribution of up to ~200 microns) were similar and not statistically different at day 28 post-treatment, indicating that particle size or crystalline form does not impact the oral flea efficacy.

No adverse reactions were seen.

EXAMPLE 4

Efficacy of Spinosad Administered per os to Cats
for the Treatment and Control of Fleas
(*Ctenocephalides felis*)

Methods: Sixteen cats of both sexes and various ages were used in the study. The cats were housed individually in cages with litter boxes and were fed a commercial dry cat food ration with ad libitum access to water. The cats were allocated to each of the 4 treatment groups (4 cats per group) based on their pre-treatment flea counts from experimental infestations. Each cat received by mouth one or two gelatin capsules containing milled technical spinosad powder and were dosed at either 0, 12.5, 25 or 50 mg of spinosad per kg of body weight on day 0. Each cat was fed a small amount of moist cat food just prior to and just after receiving their individual gelatin capsules containing spinosad. Each cat was experimentally infested with ~100 unfed adult fleas on test days −1, 0 (8 hours), 2, 6, 9, 13, 20 and 27. Comb counts for live adult fleas were conducted ~24 hours following dosing or each of the subsequent experimental infestations (i.e.—test days 0 @ 8 hours, 1, 3, 7, 10, 14, 21, and 28).

Table 5 summarizes the results of this study.

TABLE 5

Geometric Mean Percent Reduction in Live Adult Flea Counts Compared to Untreated Control Group in Cats Treated Orally with Spinosad

| Spinosad, Oral Dose (mg/kg) | Hours/Days Post Treatment | | | | | | | |
|---|---|---|---|---|---|---|---|---|
| | 8 hrs. | 1 | 3 | 7 | 10 | 14 | 21 | 28 |
| 12.5 | 94.6 | 100 | 100 | 96.7 | 85.0 | 92.2 | 68.2 | 36.1 |
| 25 | 97.4 | 100 | 100 | 98.1 | 97.1 | 95.4 | 83.1 | 69.7 |
| 50 | 97.0 | 100 | 100 | 97.5 | 97.8 | 97.9 | 90.9 | 74.4 |

Summary: Orally administered spinosad provided excellent immediate knockdown efficacy (94.6 to 100% at 8 hours and on days 1 & 3 post-treatment) and also good to excellent long term post-treatment residual control of fleas on cats. The 50 mg/kg milled spinosad oral dose provided greater than 90% flea efficacy through day 21 of the study. The lower dosages of milled spinosad provided shorter post-treatment residual control based on the dose.

Adverse reactions: one cat in the 25 mg/kg dose group and 2 cats in the 50 mg/kg dose group vomited a small amount of food ~1 hour post-treatment. The cause is unknown.

EXAMPLE 5

The following is an example of a suitable tablet formulation:

| Component | Percent of Formulation by Weight |
|---|---|
| Spinosad, technical, (90%) | 5.5 |
| Microcrystalline cellulose | 20.0 |
| Compressible sugar | 30.0 |
| Carboxymethyl cellulose, sodium salt, crosslinked | 10.0 |
| Magnesium stearate | 10.0 |
| Silicon dioxide, colloidal | 20.0 |
| Tuna (fish) flavoring | 4.5 |
| | 100.0 |

Each tablet contains 5% of the spinosyn component by weight.

EXAMPLE 6

The following is an example of a suitable liquid formulation:

| Component | Percent of Formulation by Weight |
|---|---|
| Spinosad, technical, (90%) | 5.5 |
| Water soluble dye | 1.0 |
| Methyl cellulose | 6.0 |
| Water | 83.0 |
| Fish flavoring agent | 4.5 |
| | 100.0 |

This formulation contains 5% of the spinosyn component by weight.

What is claimed is:

1. A single-dose oral formulation for controlling an ectoparasite infestation on a dog or cat comprising an ectoparasiticidal amount of spinosad, or a physiologically acceptable derivative or salt thereof, and a physiologically acceptable carrier in a systemically effective oral dosage form selected from tablet, capsule or liquid suitable for administration once every at least 7 days at a dose of 10 to 100 mg of spinosad per kg of body weight.

2. A formulation of claim 1 wherein the dosage form is a tablet and the amount of the spinosad is from 1 to 75 percent by weigth of the tablet.

3. A formulation of claim 1 which is administered once every two weeks.

4. A formulation of claim 1 which is administered once every 30 days.

5. A single-dose oral formulation for controlling an ectoparasite infestation on a dog or cat comprising an ectoparasiticidal amount of spinosad, or a physiologically acceptable derivative or salt thereof, and a physiologically acceptable carrier in a systemically effective chewable treat oral dosage form suitable for administration once every at least 7 days at a dose of 10 to 100 mg of spinosad per kg of body weight.

6. A formulation of claim 5 which is administered once every two weeks.

7. A formulation of claim 5 which is administered once every 30 days.

* * * * *